(12) United States Patent
Ascione et al.

(10) Patent No.: US 7,204,855 B2
(45) Date of Patent: Apr. 17, 2007

(54) COMPOSITIONS COMPRISING A CATIONIC HOMOPOLYMER AND THEIR USE FOR STABILIZATION OF AN OXIDIZING SOLUTION

(75) Inventors: Jean-Marc Ascione, New York, NY (US); Michael De George, Toms River, NJ (US)

(73) Assignee: L'Oreal S.A. (FR)

( * ) Notice: Subject to any disclaimer, the term of this patent is extended or adjusted under 35 U.S.C. 154(b) by 926 days.

(21) Appl. No.: 09/881,807

(22) Filed: Jun. 18, 2001

(65) Prior Publication Data

US 2003/0009834 A1  Jan. 16, 2003

(51) Int. Cl.
*D06L 3/00* (2006.01)

(52) U.S. Cl. .................. 8/101; 8/107; 8/111; 424/70.1; 424/70.2; 424/70.6; 424/70.11; 424/70.122; 424/70.16; 424/70.28; 424/70.31

(58) Field of Classification Search ............... 424/70.1, 424/70.2, 70.6, 70.11, 70.122, 70.16, 70.28, 424/70.31, 70.38; 8/516, 521, 606, 611, 8/101, 107, 111
See application file for complete search history.

(56) References Cited

U.S. PATENT DOCUMENTS

| | | | |
|---|---|---|---|
| 4,806,345 A | | 2/1989 | Bhattacharyya ............... 424/70 |
| 5,009,880 A | * | 4/1991 | Grollier et al. ............... 424/47 |
| 5,735,908 A | * | 4/1998 | Cotteret et al. ................ 8/410 |
| 5,958,397 A | * | 9/1999 | Smerbeck et al. ....... 424/78.03 |
| 6,156,076 A | * | 12/2000 | Casperson et al. ............. 8/406 |
| 6,315,989 B1 | * | 11/2001 | Narasimhan et al. ......... 424/62 |

FOREIGN PATENT DOCUMENTS

| | | |
|---|---|---|
| EP | 1 031 343 A1 | 8/2000 |
| EP | 1 106 167 A2 | 6/2001 |
| WO | WO 01/41723 A1 | 6/2001 |

* cited by examiner

*Primary Examiner*—Eisa Elhilo
(74) *Attorney, Agent, or Firm*—Finnegan, Henderson, Farabow, Garrett, & Dunner, LLP

(57) ABSTRACT

Compositions comprising (a) at least one cationic homopolymer comprising repeating units of formula (I); (b) at least one fatty alcohol; (c) at least one alkoxylated fatty alcohol; (d) at least one fatty amide; and (e) at least one oxidizing agent, and methods using the same to provide physical stability to an oxidizing composition, and in treatment compositions for keratinous fibers.

168 Claims, No Drawings

COMPOSITIONS COMPRISING A CATIONIC HOMOPOLYMER AND THEIR USE FOR STABILIZATION OF AN OXIDIZING SOLUTION

The present invention relates to compositions comprising (a) at least one cationic homopolymer comprising repeating units as described below, (b) at least one fatty alcohol, (c) at least one alkoxylated fatty alcohol, (d) at least one fatty amide, and (e) at least one oxidizing agent. The compositions of the invention may, in one embodiment, provide physically stable oxidizing compositions and may be useful in, for example, a process such as dyeing, bleaching, relaxing, and permanent waving of keratinous fibers. Keratinous fibers may be chosen from human keratinous fibers, such as hair, eyelashes, and eyebrows. The present invention also provides methods for providing physical stability to an oxidizing composition.

It is very popular to treat keratinous fibers, for example human hair, with various chemical hair treatments such as dyeing, bleaching, permanent waving, or relaxing/straightening. Normally these chemical treatments involve the use of an oxidizing composition.

Hair fiber, a keratinous material, is comprised of proteins (polypeptides), many of which are bonded together by disulfide bonds (—S—S—). A disulfide bond may be formed from the reaction of two sulfhydryl groups (—SH), one on each of two cysteine residues, which results in the formation of a cystine residue. While there may be other types of bonds which occur between the polypeptides in hair fibers, such as salt (ionic) bonds, the permanent curling or the shape of the hair is generally dependent on the disulfide bonds of cystine residues.

As a result, relaxing or straightening of hair can be achieved by disrupting the disulfide bonds of the hair fibers with an alkaline or a reducing agent. The chemical disruption of disulfide bonds by an alkaline agent is usually combined with mechanical straightening of the hair, such as combing, and straightening generally occurs due to changes in the relative positions of opposing polypeptide chains within the hair fiber. The reaction is generally terminated by rinsing and/or the application of a neutralizing composition, such as an oxidizing composition.

A similar example of a chemical treatment that utilizes an oxidizing composition is permanent waving. Hair that has been treated with a reducing agent to break the hair's disulfide bonds can be neutralized with an oxidizing composition to stop the reducing process so the bonds can re-form to cause wavy or curly hair.

Hair dyes also may utilize an oxidizing composition, such as hydrogen peroxide, in combination with a dye containing solution to provide an oxygen source for lifting natural pigment and/or for synthetic dye oxidation.

When formulating an oxidizing composition, however, one faces the challenges of chemical stability of the oxidizing agent and physical stability of the oxidizing composition. The physical stability, for example, may be important to insure a homogeneous oxidizing activity. A non-homogeneous oxidizing composition may lead to variation in oxidizing activity that may result in problems with safety and/or performance, and/or variation in viscosity that may also result in performance issues.

Thus, in some applications there may be a need for oxidizing compositions that are physically stable and may be used in conjunction with popular chemical treatments for keratinous fibers. The inventors have found that the use of at least one cationic homopolymer, at least one fatty alcohol, at least one alkoxylated fatty alcohol, and at least one fatty amide in an oxidizing composition may, for example, result in a physically stable composition.

In one embodiment, the invention provides a composition comprising (a) at least one cationic homopolymer comprising repeating units of formula (I), (b) at least one fatty alcohol, (c) at least one alkoxylated fatty alcohol, (d) at least one fatty amide, and (e) at least one oxidizing agent. Formula (I) is defined as follows:

$R_1$, $R_2$ and $R_3$, which may be identical or different, are each chosen from H, alkyl groups, and alkenyl groups; and $R_4$ is chosen from groups comprising at least one quaternary amino group.

The at least one cationic homopolymer, the at least one fatty alcohol, the at least one alkoxylated fatty alcohol, the at least one fatty amide, and the at least one oxidizing agent may be present in a combined amount effective to provide a physically stable composition. Note that as used herein, "at least one" means one or more and thus includes individual components as well as mixtures/combinations.

Also note that as used herein, the term "alkyl group" refers to substituted linear alkyl groups, unsubstituted linear alkyl groups, substituted branched alkyl groups, unsubstituted branched alkyl groups, substituted cyclic alkyl groups and unsubstituted cyclic alkyl groups, wherein the alkyl groups comprise at least one carbon and may optionally further comprise at least one heteroatom intercalated in the alkyl chain. Non-limiting examples of alkyl groups include methyl, methyl ethyl ether, and diethyl amine. Further, as used herein, "alkylene group" refers to substituted linear alkylene groups, unsubstituted linear alkylene groups, substituted branched alkylene groups, unsubstituted branched alkylene groups, substituted cyclic alkylene groups and unsubstituted cyclic alkylene groups, wherein the alkylene groups comprise at least one carbon and may optionally further comprise at least one heteroatom intercalated in the alkylene chain. Similarly, as used herein, the term "alkenyl group" refers to substituted linear alkenyl groups, unsubstituted linear alkenyl groups, substituted branched alkenyl groups, unsubstituted branched alkenyl groups, substituted cyclic alkenyl groups and unsubstituted cyclic alkenyl groups, wherein the alkenyl groups comprise at least one carbon and at least one double bond, and may optionally further comprise at least one heteroatom intercalated in the alkenyl chain. Further, as used herein, the term "alkenylene group" refers to substituted linear alkenylene groups, unsubstituted linear alkenylene groups, substituted branched alkenylene groups, unsubstituted branched alkenylene groups, substituted cyclic alkenylene groups and unsubstituted cyclic alkenylene groups, wherein the alkenylene groups comprise at least one carbon and at least one double bond, and may optionally further comprise at least one heteroatom intercalated in the alkenylene chain.

The invention also provides a method for providing physical stability to an oxidizing composition comprising including in the oxidizing composition (a) at least one cationic homopolymer comprising repeating units of formula (I), (b) at least one fatty alcohol, (c) at least one alkoxylated fatty alcohol, and (d) at least one fatty amide. As defined herein, an "oxidizing composition" comprises at least one oxidizing agent. The at least one cationic homopolymer, at least one fatty alcohol, at least one alkoxylated fatty alcohol, and at least one fatty amide are present in a combined amount effective to provide stability to the oxidizing composition.

The invention also provides a method for treating keratinous fibers comprising applying to the keratinous fibers at least one treatment composition comprising an oxidizing composition, wherein the oxidizing composition comprises (a) at least one cationic homopolymer comprising repeating units of formula (I); (b) at least one fatty alcohol; (c) at least one alkoxylated fatty alcohol; and (d) at least one fatty amide. In one embodiment, keratinous fibers are chosen from human keratinous fibers, such as hair, eyelashes, and eyebrows.

Yet another subject of the present invention is a multi-compartment kit for the chemical treatment of keratinous fibers, wherein the kit has at least two separate compartments. The first compartment contains an oxidizing composition comprising at least one cationic homopolymer comprising repeating units of formula (I), at least one fatty alcohol, at least one alkoxylated fatty alcohol, and at least one fatty amide. The second compartment contains a composition for chemical treatment of the fibers. In one embodiment, keratinous fibers are chosen from human keratinous fibers, such as, hair, eyelashes, and eyebrows.

It is to be understood that both the foregoing general description and the following detailed description are exemplary and explanatory only and are not restrictive of the invention as claimed.

Another subject of the invention is an oxidizing composition which may be useful in the chemical treatment of keratinous material, such as, for example, dyeing, bleaching, relaxing, and permanent waving of keratinous fibers. In one embodiment, the compositions of the invention are physically stable. Keratinous fibers may be chosen from human keratinous fibers, such as hair, eyelashes, and eyebrows.

As used herein, "physical stability" is evaluated by placing the composition in a controlled environment chamber for 8 weeks at 45° C. In this evaluation, the viscosity of a sample composition is measured prior to placing the sample in the chamber. For example, the viscosity may be measured at 25° C. using a Rheomat RM 180, Spindle # 3, Shear 200, for 60 seconds. Following 8 weeks in the controlled environment chamber at 45° C., the sample is removed from the chamber and the viscosity of the sample is measured using the same equipment and parameters for the initial viscosity determination, i.e., at 25° C. using a Rheomat RM 180, Spindle # 3, Shear 200, for 60 seconds. The change in viscosity after 8 weeks in the controlled environment chamber is noted. A composition is considered to lack physical stability if a decrease in viscosity of more than 20% is observed. Thus, as used herein, "stabilization" means making a composition "physically stable".

As described above, the at least one cationic homopolymer of the present invention comprises repeating units of formula (I)

wherein:
  $R_1$, $R_2$, and $R_3$, which may be identical or different, are each chosen from H, alkyl groups, and alkenyl groups; and
  $R_4$ is chosen from groups comprising at least one quaternary amino group.

The alkyl groups of $R_1$, $R_2$, and $R_3$ may be chosen from linear alkyl groups, branched alkyl groups and cyclic alkyl groups, e.g., $C_1$ to $C_{20}$ alkyl groups, and may optionally be substituted. Similarly, the alkenyl groups of $R_1$, $R_2$, and $R_3$ may be chosen from linear alkenyl groups, branched alkenyl groups and cyclic alkenyl groups, e.g., $C_1$ to $C_{20}$ alkenyl groups, and may optionally be substituted. In one embodiment, $R_1$, $R_2$, and $R_3$ are each H, while in another embodiment, $R_1$ and $R_2$ are each H, and $R_3$ is $CH_3$.

As used herein, "substituted" means comprising at least one substituent. Non-limiting examples of substituents include atoms, such as oxygen atoms and nitrogen atoms, as well as functional groups, such as hydroxyl groups, ether groups, oxyalkylene groups, polyoxyalkylene groups, carboxylic acid groups, amine groups, amide groups, halogen containing groups, ester groups, siloxane groups, and polysiloxane groups. Thus, as used herein, substituted alkyl groups comprise, for example, hydroxylated alkyl groups (R—OH).

In one embodiment, in the definition of $R_4$, the groups comprising at least one quaternary amino group may be chosen from compounds of formula (II):

wherein:
  $R_5$, $R_6$ and $R_7$, which may be identical or different, are each chosen from H, alkyl groups, and alkenyl groups; and
  $R_8$ is chosen from alkylene groups and alkenylene groups.

The alkyl groups of $R_5$ to $R_7$ may be chosen from linear $C_1$ to $C_{20}$ alkyl groups, branched $C_1$ to $C_{20}$. alkyl groups and cyclic $C_1$ to $C_{20}$ alkyl groups, wherein the $C_1$ to $C_{20}$ alkyl groups may optionally be substituted. The alkenyl groups of $R_5$ to $R_7$ may be chosen from linear $C_1$ to $C_{20}$ alkenyl groups, branched $C_1$ to $C_{20}$ alkenyl groups and cyclic $C_1$ to $C_{20}$ alkenyl groups, wherein the $C_1$ to $C_{20}$ alkenyl groups may optionally be substituted. The alkylene groups of $R_8$ may be chosen from linear $C_1$ to $C_{20}$ alkylene groups, branched $C_1$ to $C_{20}$ alkylene groups and cyclic $C_1$ to $C_{20}$ alkylene groups, wherein the $C_1$ to $C_{20}$ alkylene groups may optionally be substituted. The alkenylene groups of $R_8$ may be chosen from linear $C_1$ to $C_{20}$ alkenylene groups, branched $C_1$ to $C_{20}$ alkenylene groups and cyclic $C_1$ to $C_{20}$ alkenylene groups, wherein the $C_1$ to $C_{20}$ alkenylene groups may optionally be substituted.

Further, in one embodiment, $R_5$ is a methyl group, $R_6$ is a methyl group, $R_7$ is an alkyl group chosen from linear $C_2$ to $C_{10}$ alkyl groups, and $R_8$ is an alkylene group chosen from linear $C_2$ to $C_{10}$ alkylene groups; while in another embodiment, $R_5$, $R_6$, and $R_7$ are each a methyl group, and $R_8$ is an alkylene group chosen from linear $C_2$ to $C_{10}$ alkylene groups, branched $C_2$ to $C_{10}$ alkylene groups, and cyclic $C_2$ to $C_{10}$ alkylene groups. For example, the groups comprising at least one quaternary amino group may be chosen from, for example, $(CH_3)_3N^+—CH_2—$, $(CH_3)_3N^+—(CH_2)_2—$, $(CH_3)_3 N^+—(CH_2)_3—$, and $(CH_3)_3N^+—(CH_2)_4—$.

In one embodiment, therefore, the at least one cationic homopolymer may be derived from polymerization of a monomer chosen from, for example, acrylic acid and methacrylic acid, followed by formation of an ester via the reaction of the carboxylic acid groups of the resultant homopolymer with at least one quaternium amino alcohol, such as $C_1$ to $C_{20}$ alkyl quaternary amino alcohols.

Non-limiting examples of at least one cationic homopolymer which may be used in the composition according to the present invention include the polyquaternium-37 family of homopolymers, which are sold by Allied Colloids under the names Salcare SC95 and Salcare SC96.

As used herein, "fatty alcohol" refers to any alcohol with a carbon chain of $C_5$ or greater, such as, for example, $C_8$ or greater, $C_{10}$ or greater, and $C_{12}$ or greater. The at least one fatty alcohol may be chosen from, for example, $C_9$–$C_{11}$ alcohols, $C_{12}$–$C_{13}$ alcohols, $C_{12}$–$C_{15}$ alcohols, $C_{12}$–$C_{16}$ alcohols, $C_{14}$–$C_{15}$ alcohols, arachidyl alcohol, behenyl alcohol, caprylic alcohol, cetearyl alcohol, cetyl alcohol, coconut alcohol, decyl alcohol, hydrogenated tallow alcohol, jojoba alcohol, lauryl alcohol, myristyl alcohol, oleyl alcohol, palm alcohol, palm kernel alcohol, stearyl alcohol, tallow alcohol, and tridecyl alcohol.

As used herein, "alkoxylated fatty alcohol" refers to any fatty alcohol with a carbon chain of $C_5$ or greater, as defined above, further comprising at least one alkoxy group. For example, the at least one alkoxylated fatty alcohol may have a carbon chain of $C_8$ or greater, $C_{10}$ or greater, and $C_{12}$ or greater. Further, for example, the at least one alkoxylated fatty alcohol may be chosen from alkoxylated polymers (including co-, ter- and homo-polymers) derived from alcohols such as glycerol (e.g. polyglyceryl derived from four glycerol molecules). The at least one alkoxy group of the at least one alkoxylated fatty alcohol may, for example, be derived from an alkoxylation reaction carried out with alkylene oxide. Non-limiting examples of at least one alkoxylated fatty alcohol include any fatty alcohol comprising at least one polyethylene glycol ether and any fatty alcohol comprising at least one polypropylene glycol ether. In one embodiment, the at least one alkoxylated fatty alcohol is chosen from ethoxylated fatty alcohols of the formula

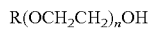

wherein:
R is chosen from: linear alkyl groups comprising at least 5 carbon atoms, branched alkyl groups comprising at least 5 carbon atoms, and cyclic alkyl groups comprising at least 5 carbon atoms, wherein the alkyl groups are optionally substituted; and linear alkenyl groups comprising at least 5 carbon atoms, branched alkenyl groups comprising at least 5 carbon atoms, and cyclic alkenyl groups comprising at least 5 carbon atoms, optionally substituted; and n is the number of ethoxy groups.

For example, n generally ranges from 2 to 100. R, for example, may be chosen from $C_8$ to $C_{22}$ alkyl groups and $C_8$ to $C_{22}$ alkenyl groups.

In one embodiment, the at least one alkoxylated fatty alcohol is chosen from alkoxy esters of polyglyceryl, such as those of the formula

and those of formula

wherein:
R is chosen from: linear alkyl groups comprising at least 5 carbon atoms, branched alkyl groups comprising at least 5 carbon atoms, and cyclic alkyl groups comprising at least 5 carbon atoms, wherein the alkyl groups are optionally substituted; and linear alkenyl groups comprising at least 5 carbon atoms, branched alkenyl groups comprising at least 5 carbon atoms, and cyclic alkenyl groups comprising at least 5 carbon atoms, wherein the alkenyl groups are optionally substituted;

R' is chosen from H; linear alkyl groups comprising at least 5 carbon atoms, branched alkyl groups comprising at least 5 carbon atoms, and cyclic alkyl groups comprising at least 5 carbon atoms, wherein the alkyl groups are optionally substituted; and linear alkenyl groups comprising at least 5 carbon atoms, branched alkenyl groups comprising at least 5 carbon atoms, and cyclic alkenyl groups comprising at least 5 carbon atoms, wherein the alkenyl groups are optionally substituted; and n is the number of glycerol groups;

with the proviso that at least one of the R' is chosen from linear alkyl groups comprising at least 5 carbon atoms, branched alkyl groups comprising at least 5 carbon atoms, and cyclic alkyl groups comprising at least 5 carbon atoms and linear alkenyl groups comprising at least 5 carbon atoms, branched alkenyl groups comprising at least 5 carbon atoms, and cyclic alkenyl groups comprising at least 5 carbon atoms.

For example, n generally ranges from 1 to 30, such as from 1 to 10. Further, for example, R and R', which may be identical or different, may be chosen from linear $C_8$ to $C_{22}$ alkyl groups, branched $C_8$ to $C_{22}$ alkyl groups, cyclic $C_8$ to $C_{22}$ alkyl groups, linear $C_8$ to $C_{22}$ alkenyl groups, branched $C_8$ to $C_{22}$ alkenyl groups, and cyclic $C_8$ to $C_{22}$ alkenyl groups.

Non-limiting examples of the at least one alkoxylated fatty alcohol include ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, cetearel:h-33, ceteareth-34, ceteareth-40, ceteareth-50, ceteareth-55, ceteareth-60, ceteareth-80, ceteareth-100, laureth-1, laureth-2, laureth-3, laureth-4, laureth-5, laureth-6, laureth-7, laureth-8, laureth-9, laureth-10, laureth-11, laureth-12, laureth-13, laureth-14, laureth-15, laureth-16, laureth-20, laureth-23, laureth-25, laureth-30, laureth-40, deceth-3, deceth-5, oleth-5, oleth-30, steareth-2, steareth-10, steareth-20, steareth-100, cetylsteareth-12, ceteareth-5, cetearetn-5, polyglyceryl 4-lauryl ether, polyglyceryl 4-oleyl ether, polyglyceryl 2-oleyl ether, polyglyceryl 2-cetyl ether, polyglyceryl 6-cetyl ether, polyglyceryl 6-oleylcetyl ether, polyglyceryl 6-octadecyl ether, $C_9$–$C_{11}$ pareth-3, $C_9$–$C_{11}$ pareth-6, $C_{11}$–$C_{15}$ pareth-3, $C_{11}$–$C_{15}$ pareth-5, $C_{11}$–$C_{15}$ pareth-12, $C_{11}$–$C_{15}$ pareth-20, $C_{12}$–$C_{15}$ pareth-9, $C_{12}$–$C_{15}$ pareth-12, and $C_{22}$–$C_{24}$ pareth-33.

As used herein, "fatty amide" refers to any amide with at least one carbon chain of $C_5$ or greater. In one embodiment, the at least one fatty amide is chosen from fatty amides of the formula

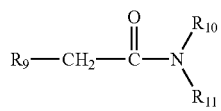

wherein:

$R_9$ is chosen from linear alkyl groups comprising at least 4 carbon atoms, branched alkyl groups comprising at least 4 carbon atoms, and cyclic alkyl groups comprising at least 4 carbon atoms, wherein the alkyl groups are optionally substituted; linear alkenyl groups comprising at least 4 carbon atoms, branched alkenyl groups comprising at least 4 carbon atoms, and cyclic, alkenyl groups comprising at least 4 carbon atoms, wherein the alkenyl groups are optionally substituted; and alkoxylated alkyl groups of formulae

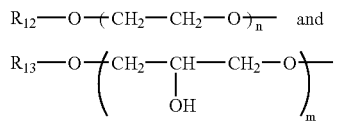

wherein:

$R_{12}$ and $R_{13}$, which may be identical or different, are each chosen from linear alkyl groups comprising at least 4 carbon atoms, branched alkyl groups comprising at least 4 carbon atoms, and cyclic alkyl groups comprising at least 4 carbon atoms, wherein the alkyl groups are optionally substituted; and linear alkenyl groups comprising at least 4 carbon atoms, branched alkenyl groups comprising at least 4 carbon atoms, and cyclic alkenyl groups comprising at least 4 carbon atoms, wherein the alkenyl groups are optionally substituted;

n ranges from 1 to 10; and m ranges from 1 to 6; and $R_{10}$ and $R_{11}$, which may be identical or different, are each chosen from H; linear alkyl groups, branched alkyl groups and cyclic alkyl groups, wherein the alkyl groups are optionally substituted; and linear alkenyl groups, branched alkenyl groups and cyclic alkenyl groups, wherein the alkenyl groups are optionally substituted.

In one embodiment, $R_9$ is chosen from linear $C_8$ to $C_{22}$ alkyl groups, branched $C_8$ to $C_{22}$ alkyl groups and cyclic $C_8$ to $C_{22}$ alkyl groups, wherein the $C_8$ to $C_{22}$ alkyl groups are optionally substituted; and linear $C_8$ to $C_{22}$ alkenyl groups, branched $C_8$ to $C_{22}$ alkenyl groups and cyclic $C_8$ to $C_{22}$ alkenyl groups, wherein the $C_8$ to $C_{22}$ alkenyl groups are optionally substituted. In another embodiment, $R_{10}$ and $R_{11}$ are each chosen from linear $C_1$ to $C_{22}$ alkyl groups, branched $C_1$ to $C_{22}$ alkyl groups and cyclic $C_1$ to $C_{22}$ alkyl groups, wherein the $C_1$ to $C_{22}$ alkyl groups are optionally substituted; and linear $C_1$ to $C_{22}$ alkenyl groups, branched $C_1$ to $C_{22}$ alkenyl groups and cyclic $C_1$ to $C_{22}$ alkenyl groups, wherein the $C_1$ to $C_{22}$ alkenyl groups are optionally substituted. In yet another embodiment, at least one of $R_{10}$ and $R_{11}$ is chosen from linear alkyl groups, branched alkyl groups and cyclic alkyl groups; and linear $C_1$ to $C_{22}$ alkenyl groups, branched $C_1$ to $C_{22}$ alkenyl groups and cyclic $C_1$ to $C_{22}$ alkenyl groups, wherein the alkyl groups and the alkenyl groups are substituted with at least one hydroxyl group. In yet another embodiment, at least one of $R_{10}$ and $R_{11}$ is chosen from linear alkyl groups, branched alkyl groups and cyclic alkyl groups; and linear $C_1$ to $C_{22}$ alkenyl groups, branched $C_1$ to $C_{22}$ alkenyl groups and cyclic $C_1$ to $C_{22}$ alkenyl groups, wherein the alkyl groups further comprise at least one ether group in the alkyl chain, and further wherein the alkenyl groups further comprise at least one ether group in the alkenyl chain.

The at least one fatty amide may be chosen from, for example, behenamide, cetyl-PG hydroxyethyl decanamide, cetyl-PG hydroxyethyl palmitamide, cocamide, dibutyl lauroyl glutamide, distearyl phthalic acid amide, lauramide, lauroyl methyl glucamide, myristoyl-PG hydroxyethyl decanamide, oleyl palmitamide, stearamide, tallow amide, trideceth-2 carboxamide monoethanolamine (tricleceth-2 carboxamide MEA), trideceth-2 carboxamide diethanolamine (trideceth-2 carboxamide DEA), and trideceth-2 carboxamide monoisopropanolamine (trideceth-2 carboxamide MIPA). Further, the at least one fatty amide may be chosen from polyalkoxylated fatty amides such as, for example, polyethoxylated fatty amides (e.g., polyethoxylated fatty amides comprising from 2 to 30 ethoxy groups) and polyglycerylated fatty amides (e.g., polyglycerylated fatty amides derived from 1 to 5 glycerol molecules).

As described above, in one embodiment, the at least one cationic homopolymer, the at least one fatty alcohol, the at least one alkoxylated fatty alcohol, and the at least one fatty amide may be present in a combined amount effective to stabilize the oxidizing composition. In one embodiment, the inventive composttition is physically stable.

One of ordinary skill in the art, armed with the physical stability test described herein, may choose the concentrations of the at least one cationic homopolymer, the at least one fatty alcohol, the at least one alkoxylated fatty alcohol, and the at least one fatty amide, including their relative concentrations, based on the physical stability desired, the viscosity desired and the application envisaged. The skilled artisan may also use the physical stability test to choose the combination of the at least one cationic homopolymer, the at least one fatty alcohol, the at least one alkoxylated fatty alcohol, and the at least one fatty amide which results in the desired stability and viscosity for the application.

In one embodiment, the at least one cationic homopolymer may be present in the composition in an amount generally ranging from 0.05% to 10% by weight relative to the total weight of the composition, such as from 0.1% to 5% by weight, and further such as from 0.25% to 2.5% by weight. The other components of the present invention may be present in the following amounts: the at least one fatty alcohol may be present in the composition, for example, in an amount generally ranging from 0.05% to 10% by weight relative to the total weight of the composition, such as from 0.1% to 8% by weight, and further such as from 0.2% to 4% by weight; the at least one alkoxylated fatty alcohol may be present in the composition, for example, in an amount generally ranging from 0.05% to 10% by weight relative to the total weight of the composition, such as from 0.1% to 5% by weight, and further such as from 0.2% to 2% by weight; and the at least one fatty amide may be present in the composition, for example, in an amount generally ranging from 0.05% to 10% by weight relative to the total weight of the composition, such as from 0.1% to 8% by weight, and further such as from 0.2% to 4% by weight.

In one embodiment, the at least one oxidizing agent of the present invention may be chosen from any oxidizing agent that is known in the art for use with the chemical treatment of keratinous materials. For example, the at least one oxidizing agent may be chosen from hydrogen peroxides, bromate salts, percarbonate salts, perborate salts and enzymes. The at least one oxidizing agent may be present in the composition in an amount generally ranging from 0.1% to 20% by weight relative to the total weight of the composition, such as from 0.5% to 12.0% .

The composition of the present invention can also contain various adjuvants conventionally used in compositions for treating the hair, such as, but not limited to, adjuvants chosen from anionic surfactants; cationic surfactants; nonionic surfactants other than the at least one alkoxylated fatty alcohol, the at least one fatty alcohol, and the at least one fatty amide; amphoteric surfactants; anionic polymers; cationic polymers other than the at least one cationic homopolymer comprising repeating units of formula (I); nonionic polymers; amphoteric polymers other than the at least one cationic homopolymer comprising repeating units of formula (I); inorganic thickeners; organic thickeners; conditioners; chelating agents; antioxidants; stabilizing agents; propellants; sequestering agents; emollients; humectants; fragrances; acidifying agents; basifying agents; moisturizing agents; vitamins; essential fatty acids; proteins; protein derivatives; preservatives; and opacifiers. Needless to say, a person skilled in the art will take care to select optional adjuvants such that the advantageous properties intrinsically associated with the invention are not, or are not substantially, adversely affected by the addition(s) envisaged.

The compositions of the present invention may be in a form, for example, chosen from an aqueous emulsion, a suspension, a dispersion, a gel, a spray, an aerosol foam, a cream, a lotion, a solution, a paste, and a hydroalcoholic lotion.

The invention also provides a method for providing physical stability to an oxidizing composition comprising including in the oxidizing composition at least one cationic homopolymer comprising repeating units of formula (I) as described above, at least one fatty alcohol, at least one alkoxylated fatty alcohol, and at least one fatty amide. The at least one cationic homopolymer, at least one fatty alcohol, at least one alkoxylated fatty alcohol, and at least one fatty amide are present in a combined amount effective to provide physical stability to the oxidizing composition.

The invention also provides al method for treating keratinous fibers comprising applying to the keratinous fibers at least one treatment composition comprising an oxidizing composition, wherein the oxidizing composition comprises at least one cationic homopolymer comprising repeating units of formula (I), at least one fatty alcohol, at least one alkoxylated fatty alcohol, and at least one fatty amide. In one embodiment, the at least one treatment composition is physically stable. In one embodiment, the at least one treatment composition is chosen from a dyeing composition, a bleaching composition, a permanent waving composition, and a relaxing/straightening composition.

Yet another subject of the present invention is a multi-compartment kit for the chemical treatment of keratinous fibers, wherein the kit has at least two separate compartments. The first compartment contains an oxidizing composition comprising at least one cationic homopolymer comprising repeating units of formula as described above, at least one fatty alcohol, and at least one alkoxylated fatty alcohol, at least one fatty amide, and at least one oxidizing agent. The second compartment contains a composition for chemical treatment of the fibers, e.g., dyeing, bleaching, permanent waving or relaxing.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result. The percentages are given on a weight basis.

EXAMPLE 1

Stabilization of an Oxidizing Composition

Compositions

Two oxidizing compositions $A_1$, and $A_2$ were prepared. Compositions $A_1$ and $A_2$ each contained hydrogen peroxide, a cationic homopolymer (polymer I and polymer II, respectively), at least one fatty alcohol, at least one alkoxylated fatty alcohol, and at least one fatty amide. Amounts shown in the table are in percent by weight.

| CTFA NAME | Composition $A_1$ | Composition $A_2$ |
|---|---|---|
| Ceteraryl alcohol | 3.2 | 3.2 |
| Ceteareth-30 | 0.8 | 0.8 |
| Trideceth-2-carboxamide MEA* | 1.2 | 1.2 |
| Glycerin | 3 | 3 |
| Tetrasodium pyrophosphate | 0.02 | 0.02 |
| Sodium stannate | 0.04 | 0.04 |
| Chelating agent | 0.15 | 0 15 |
| Hydrogen peroxide (50%) | 4.4 | 4.4 |
| POLYMER I (polyquaternium 37, mineral oil, and PPG-1 trideceth-6) | 1.5 | — |
| POLYMER II (polyquaternium 37, propylene glycol dicaprylate dicaprate, and PPG-1 trideceth-6) | — | 1.5 |
| Conditioning agents | 3 | 3 |
| Acidic pH adjuster | Q.S. to pH 2.8 (+/− 0.3) | Q.S. to pH 2.8 (+/− 0.3) |
| Water | Q.S. to 100 | Q.S. to 100 |

*Available from Kao Chemicals GmbH as AMINOL A 15/AKYPO A 15

Results

The physical stability of oxidizing compositions $A_1$ and $A_2$ was evaluated. The initial viscosity of each sample was measured prior to placing the sample in the controlled environment chamber. The viscosity was measured at 25° C. using a Rheomat RM 180, Spindle # 3, Shear 200, for 60 seconds. Following 8 weeks in the controlled environment chamber at 45° C., the sample was removed from the chamber and the viscosity of the sample was again measured at 25° C. using a Rheomat RM 180, Spindle # 3, Shear 200, for 60 seconds. The results are shown in Table 1:

TABLE 1

|  | $A_1$ | $A_2$ |
|---|---|---|
| Initial viscosity | 46 DU | 31 DU |
| Viscosity after 8 weeks at 45° C. | 42 DU | 35 DU |

The results demonstrate that acceptable physical stability was observed for compositions $A_1$ and $A_2$ comprising at least one cationic homopolymer, at least one fatty alcohol, at least one alkoxylated fatty alcohol, at least one fatty amide, and at least one oxidizing agent.

What is claimed is:

1. A composition comprising:
  (a) at least one cationic homopolymer comprising repeating units of formula

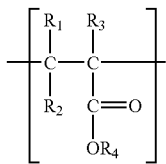

(I)

wherein:
    $R_1$, $R_2$, and $R_3$, which may be identical or different, are each chosen from H, alkyl groups, and alkenyl groups; and
    $R_4$ is chosen from groups comprising at least one quaternary amino group;
  (b) at least one fatty alcohol;
  (c) at least one alkoxylated fatty alcohol;
  (d) at least one fatty amide; and
  (e) at least one oxidizing agent.

2. The composition according to claim 1, wherein said composition is physically stable.

3. The composition according to claim 1, wherein said alkyl groups of $R_1$, $R_2$ and $R_3$ are chosen from linear $C_1$ to $C_{20}$ alkyl groups, branched $C_1$ to $C_{20}$ alkyl groups and cyclic $C_1$ to $C_{20}$ alkyl groups, and further wherein said $C_1$ to $C_{20}$ alkyl groups are optionally substituted.

4. The composition according to claim 1, wherein said alkenyl groups of $R_1$, $R_2$ and $R_3$ are chosen from linear $C_1$ to $C_{20}$ alkenyl groups, branched $C_1$ to $C_{20}$ alkenyl groups and cyclic $C_1$ to $C_{20}$ alkenyl groups, and further wherein said $C_1$ to $C_{20}$ alkenyl groups are optionally substituted.

5. The composition according to claim 1, wherein $R_1$, $R_2$, and $R_3$ are each H.

6. The composition according to claim 1, wherein $R_1$ is H, $R_2$ is H and $R_3$ is $CH_3$.

7. The composition according to claim 1, wherein, in the definition of $R_4$, said groups comprising at least one quaternary amino group are chosen from $C_1$ to $C_{20}$ alkyl quaternary amino groups.

8. The composition according to claim 1, wherein, in the definition of $R_4$, said groups comprising at least one quaternary amino group are chosen from compounds of formula (II):

(II)

wherein:
    $R_5$, $R_6$ and $R_7$, which may be identical or different, are each chosen from H, alkyl groups, and alkenyl groups; and
    $R_8$ is chosen from alkylene groups and alkenylene groups.

9. The composition according to claim 8, wherein said alkyl groups of $R_5$, $R_6$, and $R_7$ are chosen from linear $C_1$ to $C_{20}$ alkyl groups, branched $C_1$ to $C_{20}$ alkyl groups, and cyclic $C_1$ to $C_{20}$ alkyl groups, and further wherein said $C_1$ to $C_{20}$ alkyl groups are optionally substituted.

10. The composition according to claim 8, wherein said alkenyl groups of $R_5$, $R_6$, and $R_7$ are chosen from linear $C_1$ to $C_{20}$ alkenyl groups, branched $C_1$ to $C_{20}$ alkenyl groups, and cyclic $C_1$ to $C_{20}$ alkenyl groups, and further wherein said $C_1$ to $C_{20}$ alkenyl groups are optionally substituted.

11. The composition according to claim 8, wherein said alkylene groups of $R_8$ are chosen from linear $C_1$ to $C_{20}$ alkylene groups, branched $C_1$ to $C_{20}$ alkylene groups, and cyclic $C_1$ to $C_{20}$ alkylene groups, and further wherein said $C_1$ to $C_{20}$ alkylene groups are optionally substituted.

12. The composition according to claim 8, wherein said alkenylene groups of $R_8$ are chosen from linear $C_1$ to $C_{20}$ alkenylene groups, branched $C_1$ to $C_{20}$ alkenylene groups and cyclic $C_1$ to $C_{20}$ alkenylene groups, and further wherein said $C_1$ to $C_{20}$ alkenylene groups are optionally substituted.

13. The composition according to claim 8, wherein said groups comprising at least one quaternary amino group are chosen from:

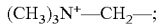

$(CH_3)_3N^+-CH_2-$;

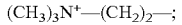

$(CH_3)_3N^+-(CH_2)_2-$;

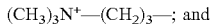

$(CH_3)_3N^+-(CH_2)_3-$; and

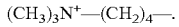

$(CH_3)_3N^+-(CH_2)_4-$.

14. The composition according to claim 8, wherein $R_5$ is a methyl group, $R_6$ is a methyl group, $R_7$ is an alkyl group chosen from linear unsubstituted $C_2$ to $C_{10}$ alkyl groups, and $R_8$ is an alkylene group chosen from linear unsubstituted $C_2$ to $C_{10}$ alkylene groups.

15. The composition according to claim 8, wherein $R_5$, $R_6$, and $R_7$ are each a methyl group, and $R_8$ is an alkylene group chosen from linear $C_2$ to $C_{10}$ alkenylene groups, branched $C_2$ to $C_{10}$ alkenylene groups and cyclic $C_2$ to $C_{10}$ alkenylene groups.

16. The composition according to claim 1, wherein said at least one cationic homopolymer is chosen from polyquaternium-37 homopolymers.

17. The composition according to claim 1, wherein said at least one fatty alcohol comprises at least 8 carbon atoms.

18. The composition according to claim 17, wherein said at least one fatty alcohol comprises at least 10 carbon atoms.

19. The composition according to claim 18, wherein said at least one fatty alcohol comprises at least 12 carbon atoms.

20. The composition according to claim 1, wherein said at least one fatty alcohol is chosen from $C_9$–$C_{11}$ alcohols, $C_{12}$–$C_{13}$ alcohols, $C_{12}$–$C_{15}$ alcohols, $C_{12}$–$C_{16}$ alcohols, and $C_{14}$–$C_{15}$ alcohols.

21. The composition according to claim 1, wherein said at least one fatty alcohol is chosen from arachidyl alcohol, behenyl alcohol, caprylic alcohol, cetearyl alcohol, cetyl alcohol, coconut alcohol, decyl alcohol, hydrogenated tallow alcohol, jojoba alcohol, lauryl alcohol, myristyl alcohol, oleyl alcohol, palm alcohol, palm kernel alcohol, stearyl alcohol, tallow alcohol, and tridecyl alcohol.

22. The composition according to claim 1, wherein said at least one alkoxylated fatty alcohol is chosen from fatty alcohols comprising at least one polyethylene glycol ether.

23. The composition according to claim 1, wherein said at least one alkoxylated fatty alcohol comprises at least 8 carbon atoms.

24. The composition according to claim 23, wherein said at least one alkoxylated fatty alcohol comprises at least 10 carbon atoms.

25. The composition according to claim 24, wherein said at least one alkoxylated fatty alcohol comprises at least 12 carbon atoms.

26. The composition according to claim 1, wherein said at least one alkoxylated fatty alcohol is chosen from ethoxylated fatty alcohols of the formula $$R(OCH_2CH_2)_nOH$$

wherein:
R is chosen from linear alkyl groups comprising at least 5 carbon atoms, branched alkyl groups comprising at least 5 carbon atoms, and cyclic alkyl groups comprising at least 5 carbon atoms, wherein said alkyl groups are optionally substituted; and linear alkenyl groups comprising at least 5 carbon atoms, branched alkenyl groups comprising at least 5 carbon atoms, and cyclic alkenyl groups comprising at least 5 carbon atoms, wherein said alkenyl groups are optionally substituted; and
n ranges from 2 to 100.

27. The composition according to claim 26, wherein R is chosen from linear $C_8$ to $C_{22}$ alkyl groups, branched $C_8$ to $C_{22}$ alkyl groups, and cyclic $C_8$ to $C_{22}$ alkyl groups.

28. The composition according to claim 26, wherein R is chosen from linear $C_8$ to $C_{22}$ alkenyl groups, branched $C_8$ to $C_{22}$ alkenyl groups, and cyclic $C_8$ to $C_{22}$ alkenyl groups.

29. The composition according to claim 1, wherein said at least one alkoxylated fatty alcohol is chosen from alkoxy esters of polyglyceryl of formula $$R(OCH_2CHOHCH_2)_nOH$$

and alkoxy esters of polyglyceryl of formula $$H(OCH_2CHOR'CH_2)_nOH$$

wherein:
R is chosen from linear alkyl groups comprising at least 5 carbon atoms, branched alkyl groups comprising at least 5 carbon atoms, and cyclic alkyl groups comprising at least 5 carbon atoms, wherein said alkyl groups are optionally substituted; and linear alkenyl groups comprising at least 5 carbon atoms, branched alkenyl groups comprising at least 5 carbon atoms, and cyclic alkenyl groups comprising at least 5 carbon atoms, wherein said alkenyl groups are optionally substituted;
R' is chosen from H; linear alkyl groups comprising at least 5 carbon atoms, branched alkyl groups comprising at least 5 carbon atoms, and cyclic alkyl groups comprising at least 5 carbon atoms, wherein said alkyl groups are optionally substituted; and linear alkenyl groups comprising at least 5 carbon atoms, branched alkenyl groups comprising at least 5 carbon atoms, and cyclic alkenyl groups comprising at least 5 carbon atoms, wherein said alkenyl groups are optionally substituted; and
n ranges from 1 to 30,
with the proviso that at least one of said R' is chosen from linear alkyl groups comprising at least 5 carbon atoms, branched alkyl groups comprising at least 5 carbon atoms, and cyclic alkyl groups comprising at least 5 carbon atoms, wherein said alkyl groups are optionally substituted, and linear alkenyl groups comprising at least 5 carbon atoms, branched alkenyl groups comprising at least 5 carbon atoms, and cyclic alkenyl groups comprising at least 5 carbon atoms, wherein said alkenyl groups are optionally substituted.

30. The composition according to claim 29, wherein R is chosen from linear $C_8$ to $C_{22}$ alkyl groups, branched $C_8$ to $C_{22}$ alkyl groups, and cyclic $C_8$ to $C_{22}$ alkyl groups.

31. The composition according to claim 29, wherein R is chosen from linear $C_8$ to $C_{22}$ alkenyl groups, branched $C_8$ to $C_{22}$ alkenyl groups, and cyclic $C_8$ to $C_{22}$ alkenyl groups.

32. The composition according to claim 1, wherein said at least one alkoxylated fatty alcohol is chosen from ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceteareth-33, ceteareth-34, ceteareth-40, ceteareth-50, ceteareth-55, ceteareth-60, ceteareth-80, ceteareth-100, laureth-1, laureth-2, laureth-3, laureth-4, laureth 5, laureth-6, laureth-7, laureth-8, laureth-9, laureth-10, laureth-11, laureth-12, laureth-13, laureth-14, laureth-15, laureth-16, laureth-20, laureth-23, laureth-25, laureth-30, laureth-40, deceth-3, deceth-5, oleth-5, oleth-30, steareth-2, steareth-10, steareth-20, steareth-100, cetylsteareth-12, ceteareth-5, ceteareth-5, polyglyceryl 4-lauryl ether, polyglyceryl 4-oleyl ether, polyglyceryl 2-oleyl ether, polyglyceryl 2-cetyl ether, polyglyceryl 6-cetyl ether, polyglyceryl 6-oleylcetyl ether, polyglyceryl 6-octadecyl ether, $C_9$–$C_{11}$ pareth-3, $C_9$–$C_{11}$ pareth-6, $C_{11}$–$C_{15}$ pareth-3, $C_{11}$–$C_{15}$ pareth-5, $C_{11}$–$C_{15}$ pareth-12, $C_{11}$–$C_{15}$ pareth-20, $C_{12}$–$C_{15}$ pareth-9, $C_{12}$–$C_{15}$ pareth-12, and $C_{22}$–$C_{24}$ pareth-33.

33. The composition according to claim 1, wherein said at least one fatty amide is chosen from fatty amides of formula

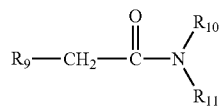

wherein:
$R_9$ is chosen from linear alkyl groups comprising at least 4 carbon atoms, branched alkyl groups comprising at least 4 carbon atoms, and cyclic alkyl groups comprising at least 4 carbon atoms, wherein said alkyl groups are optionally substituted; linear alkenyl groups comprising at least 4 carbon atoms, branched alkenyl groups comprising at least 4 carbon atoms, and cyclic alkenyl groups comprising at least 4 carbon atoms, wherein said alkenyl groups are optionally substituted; and alkoxylated alkyl groups of formulae

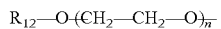

and

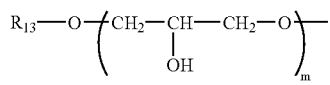

wherein:
$R_{12}$ and $R_{13}$, which may be identical or different, are each chosen from linear alkyl groups comprising at least 4 carbon atoms, branched alkyl groups comprising at least 4 carbon atoms, and cyclic alkyl groups comprising at least 4 carbon atoms, wherein said alkyl groups are optionally substituted; and linear alkenyl groups comprising at least 4 carbon atoms, branched alkenyl groups comprising at least 4 carbon atoms, and cyclic alkenyl groups comprising at least 4 carbon atoms, wherein said alkenyl groups are optionally substituted;
n ranges from 1 to 10; and
m ranges from 1 to 6; and
$R_{10}$ and $R_{11}$, which may be identical or different, are each chosen from H; linear alkyl groups, branched alkyl groups and cyclic alkyl groups, wherein said alkyl groups are optionally substituted; and linear alkenyl groups, branched alkenyl groups and cyclic alkenyl groups, wherein said alkenyl groups are optionally substituted.

34. The composition according to claim 33, wherein $R_9$ is chosen from linear $C_8$ to $C_{22}$ alkyl groups, branched $C_8$ to $C_{22}$ alkyl groups and cyclic $C_8$ to $C_{22}$ alkyl groups, wherein said $C_8$ to $C_{22}$ alkyl groups are optionally substituted; and linear $C_8$ to $C_{22}$ alkenyl groups, branched $C_8$ to $C_{22}$ alkenyl groups and cyclic $C_8$ to $C_{22}$ alkenyl groups, wherein said $C_8$ to $C_{22}$ alkenyl groups are optionally substituted.

35. The composition according to claim 33, wherein $R_{10}$ and $R_{11}$ are each chosen from linear $C_1$ to $C_{22}$ alkyl groups, branched $C_1$ to $C_{22}$ alkyl groups and cyclic $C_1$ to $C_{22}$ alkyl groups, wherein said $C_1$ to $C_{22}$ alkyl groups are optionally substituted; and linear $C_1$ to $C_{22}$ alkenyl groups, branched $C_1$ to $C_{22}$ alkenyl groups and cyclic $C_1$ to $C_{22}$ alkenyl groups, wherein said $C_1$ to $C_{22}$ alkenyl groups are optionally substituted.

36. The composition according to claim 33, wherein at least one of said $R_{10}$ and said $R_{11}$ is chosen from linear $C_1$ to $C_{22}$ alkyl groups, branched $C_1$ to $C_{22}$ alkyl groups and cyclic $C_1$ to $C_{22}$ alkyl groups; and linear $C_1$ to $C_{22}$ alkenyl groups, branched $C_1$ to $C_{22}$ alkenyl groups and cyclic $C_1$ to $C_{22}$ alkenyl groups, wherein said alkyl groups and said alkenyl groups are substituted with at least one hydroxyl group.

37. The composition according to claim 33, wherein at least one of said $R_{10}$ and said $R_{11}$ is chosen from linear $C_1$ to $C_{22}$ alkyl groups, branched $C_1$ to $C_{22}$ alkyl groups and cyclic $C_1$ to $C_{22}$ alkyl groups; and linear $C_1$ to $C_{22}$ alkenyl groups, branched $C_1$ to $C_{22}$ alkenyl groups and cyclic $C_1$ to $C_{22}$ alkenyl groups, wherein said alkyl groups further comprise at least one ether group in the alkyl chain, and further wherein said alkenyl groups further comprise at least one ether group in the alkenyl chain.

38. The composition according to claim 1, wherein said at least one fatty amide is chosen from behenamide, cetyl-PG hydroxyethyl decanamide, cetyl-PG hydroxyethyl palmitamide, cocamide, dibutyl lauroyl glutamide, distearyl phthalic acid amide, lauramide, lauroyl methyl glucamide, myristoyl-PG hydroxyethyl decanamide, oleyl palmitamide, stearamide, tallow amide, trideceth-2 carboxamide monoethanolamine (trideceth-2 carboxamide MEA), trideceth-2 carboxamide diethanolamine (trideceth-2 carboxamide DEA), trideceth-2 carboxamide monoisopropanolamine (trideceth-2 carboxamide MIPA), and polyalkoxylated fatty amides.

39. The composition according to claim 38, wherein said polyalkoxylated fatty amides are chosen from polyethoxylated fatty amides and polyglycerylated fatty amides.

40. The composition according to claim 1, wherein said at least one cationic homopolymer is present in an amount ranging from 0.05% to 10% by weight relative to the total weight of the composition.

41. The composition according to claim 40, wherein said at least one cationic homopolymer is present in an amount ranging from 0.1% to 5% by weight relative to the total weight of the composition.

42. The composition according to claim 41, wherein said at least one cationic homopolymer is present in an amount ranging from 0.25% to 2.5% by weight relative to the total weight of the composition.

43. The composition according to claim 1, wherein said at least one fatty alcohol is present in an amount ranging from 0.05% to 10% by weight relative to the total weight of the composition.

44. The composition according to claim 43, wherein said at least one fatty alcohol is present in an amount ranging from 0.1% to 8% by weight relative to the total weight of the composition.

45. The composition according to claim 44, wherein said at least one fatty alcohol is present in an amount ranging from 0.2% to 4% by weight relative to the total weight of the composition.

46. The composition according to claim 1, wherein said at least one alkoxylated fatty alcohol is present in an amount ranging from 0.05% to 10% by weight relative to the total weight of the composition.

47. The composition according to claim 46, wherein said at least one alkoxylated fatty alcohol is present in an amount ranging from 0.1% to 5% by weight relative to the total weight of the composition.

48. The composition according to claim 47, wherein said at least one alkoxylated fatty alcohol is present in an amount ranging from 0.2% to 2% by weight relative to the total weight of the composition.

49. The composition according to claim 1, wherein said at least one fatty amide is present in an amount ranging from 0.05% to 10% by weight relative to the total weight of the composition.

50. The composition according to claim 49, wherein said at least one fatty amide is present in an amount ranging from 0.1% to 8% by weight relative to the total weight of the composition.

51. The composition according to claim 50, wherein said at least one fatty amide is present in an amount ranging from 0.2% to 4% by weight relative to the total weight of the composition.

52. The composition according to claim 1, wherein said at least one oxidizing agent is chosen from hydrogen peroxides, bromate salts, percarbonate salts, perborate salts and enzymes.

53. The composition according to claim 1, wherein said at least one oxidizing agent is present in an amount ranging from 0.1% to 20.0% by weight relative to the total weight of the composition.

54. The composition according to claim 53, wherein said at least one oxidizing agent is present in an amount ranging from 0.5% to 12% by weight relative to the total weight of the composition.

55. The composition according to claim 1, further comprising at least one adjuvant chosen from anionic surfactants; cationic surfactants; nonionic surfactants other than said at least one alkoxylated fatty alcohol, said at least one fatty alcohol, and said at least one fatty amide; amphoteric surfactants; anionic polymers; cationic polymers other than said at least one cationic homopolymer comprising repeating units of formula (I); nonionic polymers; amphoteric polymers other than said at least one cationic homopolymer comprising repeating units of formula (I); inorganic thickeners; organic thickeners; conditioners; chelating agents; antioxidants; stabilizing agents; propellants; sequestering agents; emollients; humectants; fragrances; acidifying agents; basifying agents; moisturizing agents; vitamins; essential fatty acids; proteins; protein derivatives; preservatives; and opacifiers.

56. The composition according to claim 1, wherein said composition is in a form chosen from an aqueous emulsion, a suspension, a dispersion, an aerosol foam, a cream, a lotion, a solution, a paste, a gel, a spray, and a hydroalcoholic lotion.

57. A method for providing physical stability to an oxidizing composition comprising:
including in said oxidizing composition:
(a) at least one cationic homopolymer comprising repeating units of formula (I):

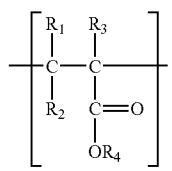

wherein:
$R_1$, $R_2$, and $R_3$, which may be identical or different, are each chosen from H, alkyl groups, and alkenyl groups; and
$R_4$ is chosen from groups comprising at least one quaternary amino group;
(b) at least one fatty alcohol;
(c) at least one alkoxylated fatty alcohol; and
(d) at least one fatty amide;
wherein said at least one cationic homopolymer, said at least one fatty alcohol, said at least one alkoxylated fatty alcohol, and said at least one fatty amide are present in a combined amount effective to provide physical stability to said oxidizing composition.

58. The method according to claim 57, wherein said alkyl groups of $R_1$, $R_2$ and $R_3$ are chosen from linear $C_1$ to $C_{20}$ alkyl groups, branched $C_1$ to $C_{20}$ alkyl groups, and cyclic $C_1$ to $C_{20}$ alkyl groups, and further wherein said $C_1$ to $C_{20}$ alkyl groups are optionally substituted.

59. The method according to claim 57, wherein said alkenyl groups of $R_1$, $R_2$ and $R_3$ are chosen from linear $C_1$ to $C_{20}$ alkenyl groups, branched $C_1$ to $C_{20}$ alkenyl groups, and cyclic $C_1$ to $C_{20}$ alkenyl groups, and further wherein said $C_1$ to $C_{20}$ alkenyl groups are optionally substituted.

60. The method according to claim 57, wherein $R_1$, $R_2$, and $R_3$ are each H.

61. The method according to claim 57, wherein $R_1$ is, H, $R_2$ is H and $R_3$ is $CH_3$.

62. The method according to claim 57, wherein, in the definition of $R_4$, said groups comprising at least one quaternary amino group are chosen from $C_1$ to $C_{20}$ alkyl quaternary amino groups.

63. The method according to claim 57, wherein, in the definition of $R_4$, said groups comprising at least one quaternary amino group are chosen from compounds of formula (II):

wherein:
$R_5$, $R_6$ and $R_7$, which may be identical or different, are each chosen from H, alkyl groups, and alkenyl groups; and
$R_8$ is chosen from alkylene groups and alkenylene groups.

64. The method according to claim 63, wherein said alkyl groups of $R_5$, $R_6$, and $R_7$ are chosen from linear $C_1$ to $C_{20}$ alkyl groups, branched $C_1$ to $C_{20}$ alkyl groups, and cyclic $C_1$ to $C_{20}$ alkyl groups, and further wherein said $C_1$ to $C_{20}$ alkyl groups are optionally substituted.

65. The method according to claim 63, wherein said alkenyl groups of $R_5$, $R_6$, and $R_7$ are chosen from linear $C_1$ to $C_{20}$ alkenyl chains, branched $C_1$ to $C_{20}$ alkenyl chains, and cyclic $C_1$ to $C_{20}$ alkenyl chains, and further wherein said $C_1$ to $C_{20}$ alkenyl groups are optionally substituted.

66. The method according to claim 63, wherein said alkylene groups of $R_8$ are chosen from linear $C_1$ to $C_{20}$ alkylene groups, branched $C_1$ to $C_{20}$ alkylene groups, and cyclic $C_1$ to $C_{20}$ alkylene groups, and further wherein said $C_1$ to $C_{20}$ alkylene groups are optionally substituted.

67. The method according to claim 63, wherein said alkenylene groups of $R_8$ are chosen from linear $C_1$ to $C_{20}$ alkenyl chains, branched $C_1$ to $C_{20}$ alkenyl chains, and cyclic $C_1$ to $C_{20}$ alkenyl chains, and further wherein said $C_1$ to $C_{20}$ alkenyl groups are optionally substituted.

68. The method according to claim 63, wherein said groups comprising at least one quaternary amino group are chosen from:

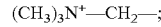

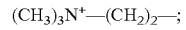

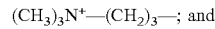

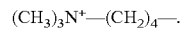

69. The method according to claim 63, wherein $R_5$ is a methyl group, $R_6$ is a methyl group, $R_7$ is an alkyl group chosen from linear unsubstituted $C_2$ to $C_{10}$ alkyl groups, and $R_8$ is an alkylene group chosen from linear unsubstituted $C_2$ to $C_{10}$ alkylene groups.

70. The method according to claim 63, wherein $R_5$, $R_6$, and $R_7$ are each a methyl group, and $R_8$ is an alkylene group chosen from $C_2$ to $C_{10}$ alkylene groups.

71. The method according to claim 57, wherein said at least one cationic homopolymer is chosen from polyquaternium-37 homopolymers.

72. The method according to claim 57, wherein said at least one fatty alcohol comprises at least 8 carbon atoms.

73. The method according to claim 72, wherein said at least one fatty alcohol comprises at least 10 carbon atoms.

74. The method according to claim 73, wherein said at least one fatty alcohol comprises at least 12 carbon atoms.

75. The method according to claim 57, wherein said at least one fatty alcohol is chosen from $C_9$–$C_{11}$ alcohols, $C_{12}$–$C_{13}$ alcohols, $C_{12}$–$C_{15}$ alcohols, $C_{12}$–$C_{16}$ alcohols, and $C_{14}$–$C_{15}$ alcohols.

76. The method according to claim 57, wherein said at least one fatty alcohol is chosen from arachidyl alcohol, behenyl alcohol, caprylic alcohol, cetearyl alcohol, cetyl alcohol, coconut alcohol, decyl alcohol, hydrogenated tallow alcohol, jojoba alcohol, lauryl alcohol, myristyl alcohol, oleyl alcohol, palm alcohol, palm kernel alcohol, stearyl alcohol, tallow alcohol, and tridecyl alcohol.

77. The method according to claim 57, wherein said at least one alkoxylated fatty alcohol is chosen from fatty alcohols comprising at least one polyethylene glycol ether.

78. The method according to claim 57, wherein said at least one alkoxylated fatty alcohol comprises at least 8 carbon atoms.

79. The method according to claim 78, wherein said at least one alkoxylated fatty alcohol comprises at least 10 carbon atoms.

80. The method according to claim 79, wherein said at least one alkoxylated fatty alcohol comprises at least 12 carbon atoms.

81. The method according to claim 57, wherein said at least one alkoxylated fatty alcohol is chosen from ethoxylated fatty alcohols of formula $R(OCH_2CH_2)_nOH$ wherein:
R is chosen from linear alkyl groups comprising at least 5 carbon atoms, branched alkyl groups comprising at least 5 carbon atoms, and cyclic alkyl groups comprising at least 5 carbon atoms, wherein said alkyl groups are optionally substituted; and linear alkenyl groups comprising at least 5 carbon atoms, branched alkenyl groups comprising at least 5 carbon atoms, and cyclic alkenyl groups comprising at least 5 carbon atoms, wherein said alkenyl groups are optionally substituted; and
n ranges from 2 to 100.

82. The method according to claim 81, wherein R is chosen from linear $C_8$ to $C_{22}$ alkyl groups, branched $C_8$ to $C_{22}$ alkyl groups, and cyclic $C_8$ to $C_{22}$ alkyl groups.

83. The method according to claim 81, wherein R is chosen from linear $C_8$ to $C_{22}$ alkenyl groups, branched $C_8$ to $C_{22}$ alkenyl groups, and cyclic $C_8$ to $C_{22}$ alkenyl groups.

84. The method according to claim 57, wherein said at least one alkoxylated fatty alcohol is chosen from alkoxy esters of polyglyceryl of formula $R(OCH_2CHOHCH_2)_nOH$ and alkoxy esters of polyglyceryl of formula $H(OCH_2CHOR'CH_2)_nOH$ R is chosen from linear alkyl groups comprising at least 5 carbon atoms, branched alkyl groups comprising at least 5 carbon atoms, and cyclic alkyl groups comprising at least 5 carbon atoms, wherein said alkyl groups are optionally substituted; and linear alkenyl groups comprising at least 5 carbon atoms, branched alkenyl groups comprising at least 5 carbon atoms, and cyclic alkenyl groups comprising at least 5 carbon atoms, wherein said alkenyl groups are optionally substituted;

R' is chosen from H; linear alkyl groups comprising at least 5 carbon atoms, branched alkyl groups comprising at least 5 carbon atoms, and cyclic alkyl groups comprising at least 5 carbon atoms, wherein said alkyl groups are optionally substituted; and linear alkenyl groups comprising at least 5 carbon atoms, branched alkenyl groups comprising at least 5 carbon atoms, and cyclic alkenyl groups comprising at least 5 carbon atoms, wherein said alkenyl groups are optionally substituted; and n ranges from 1 to 30, with the proviso that at least one of said R' is chosen from linear alkyl groups comprising at least 5 carbon atoms, branched alkyl groups comprising at least 5 carbon atoms, and cyclic alkyl groups comprising at least 5 carbon atoms, wherein said alkyl groups are optionally substituted; and linear alkenyl groups comprising at least 5 carbon atoms, branched alkenyl groups comprising at least 5 carbon atoms, and cyclic alkenyl groups comprising at least 5 carbon atoms, wherein said alkenyl groups are optionally substituted.

85. The method according to claim 84, wherein R is chosen from linear $C_8$ to $C_{22}$ alkyl groups, branched $C_8$ to $C_{22}$ alkyl groups, and cyclic $C_8$ to $C_{22}$ alkyl groups.

86. The composition according to claim 84, wherein R is chosen from linear $C_8$ to $C_{22}$ alkenyl groups, branched $C_8$ to $C_{22}$ alkenyl groups, and cyclic $C_8$ to $C_{22}$ alkenyl groups.

87. The method according to claim 57, wherein said at least one alkoxylated fatty alcohol is chosen from ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceteareth-33, ceteareth-34, ceteareth-40, ceteareth-50, ceteareth-55, ceteareth-60, ceteareth-80, ceteareth-100, laureth-1, laureth-2, laureth-3, laureth-4, laureth-5, laureth-6, laureth-7, laureth-8, laureth-9, laureth-10, laureth-11, laureth-12, laureth-13, laureth-14, laureth-15, laureth-16, laureth-20, laureth-23, laureth-25, laureth-30, laureth-40, deceth-3, deceth-5, oleth-5, oleth-30, steareth-2, steareth-10, steareth-20, steareth-100, cetylsteareth-12, ceteareth-5, ceteareth-5, polyglyceryl 4-lauryl ether, polyglyceryl 4-oleyl ether, polyglyceryl 2-oleyl ether, polyglyceryl 2-cetyl ether, polyglyceryl 6-cetyl ether, polyglyceryl 6-oleylcetyl ether, polyglyceryl 6-octadecyl ether, $C_9$–$C_{11}$ pareth-3, $C_9$–$C_{11}$ pareth-6, $C_{11}$–$C_{15}$ pareth-3, $C_{11}$–$C_{15}$ pareth-5, $C_{11}$–$C_{15}$ pareth-12, $C_{11}$–$C_{15}$ pareth-20, $C_{12}$–$C_{15}$ pareth-9, $C_{12}$–$C_{15}$ pareth-12, and $C_{22}$–$C_{24}$ pareth-33.

88. The method according to claim 57, wherein said at least one fatty amide is chosen from fatty amides of formula

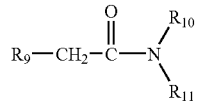

wherein:

R$_9$ is chosen from linear alkyl groups comprising at least 4 carbon atoms, branched alkyl groups comprising at least 4 carbon atoms, and cyclic alkyl groups comprising at least 4 carbon atoms, wherein said alkyl groups are optionally substituted; linear alkenyl groups comprising at least 4 carbon atoms, branched alkenyl groups comprising at least 4 carbon atoms, and cyclic alkenyl groups comprising at least 4 carbon atoms, wherein said alkenyl groups are optionally substituted; and alkoxylated alkyl groups of formulae

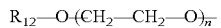

and

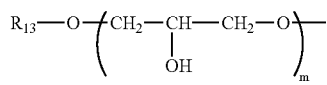

wherein:

R$_{12}$ and R$_{13}$, which may be identical or different, are each chosen from linear alkyl groups comprising at least 4 carbon atoms, branched alkyl groups comprising at least 4 carbon atoms, and cyclic alkyl groups comprising at least 4 carbon atoms, wherein said alkyl groups are optionally substituted; and linear alkenyl groups comprising at least 4 carbon atoms, branched alkenyl groups comprising at least 4 carbon atoms, and cyclic alkenyl groups comprising at least 4 carbon atoms, wherein said alkenyl groups are optionally substituted;

n ranges from 1 to 10; and m ranges from 1 to 6; and

R$_{10}$ and R$_{11}$, which may be identical or different, are each chosen from H, linear alkyl groups, branched alkyl groups and cyclic alkyl groups, wherein said alkyl groups are optionally substituted; and linear alkenyl groups, branched alkenyl groups and cyclic alkenyl groups, wherein said alkenyl groups are optionally substituted.

89. The method according to claim 88, wherein R$_9$ is chosen from linear C$_8$ to C$_{22}$ alkyl groups, branched C$_8$ to C$_{22}$ alkyl groups and cyclic C$_8$ to C$_{22}$ alkyl groups, wherein said C$_8$ to C$_{22}$ alkyl groups are optionally substituted; and linear C$_8$ to C$_{22}$ alkenyl groups, branched C$_8$ to C$_{22}$ alkenyl groups and cyclic C$_8$ to C$_{22}$ alkenyl groups, wherein said C$_8$ to C$_{22}$ alkenyl groups are optionally substituted.

90. The method according to claim 88, wherein R$_{10}$ and R$_{11}$ are each chosen from linear C$_1$ to C$_{22}$ alkyl groups, branched C$_1$ to C$_{22}$ alkyl groups and cyclic C$_1$ to C$_{22}$ alkyl groups, wherein said C$_1$ to C$_{22}$ alkyl groups are optionally substituted; and linear C$_1$ to C$_{22}$ alkenyl groups, branched C$_1$ to C$_{22}$ alkenyl groups and cyclic C$_1$ to C$_{22}$ alkenyl groups, wherein said C$_1$ to C$_{22}$ alkenyl groups are optionally substituted.

91. The method according to claim 88, wherein at least one of said R$_{10}$ and said R$_{11}$ is chosen from linear C$_1$ to C$_{22}$ alkyl groups, branched C$_1$ to C$_{22}$ alkyl groups and cyclic C$_1$ to C$_{22}$ alkyl groups; and linear C$_1$ to C$_{22}$ alkenyl groups, branched C$_1$ to C$_{22}$ alkenyl groups and cyclic C$_1$ to C$_{22}$ alkenyl groups, wherein said alkyl groups and said alkenyl groups are substituted with at least one hydroxyl group.

92. The method according to claim 88, wherein at least one of said R$_{10}$ and R$_{11}$ is chosen from linear C$_1$ to C$_{22}$ alkyl groups, branched C$_1$ to C$_{22}$ alkyl groups and cyclic C$_1$ to C$_{22}$ alkyl groups, and linear C$_1$ to C$_{22}$ alkenyl groups, branched C$_1$ to C$_{22}$ alkenyl groups and cyclic C$_1$ to C$_{22}$ alkenyl groups, wherein said alkyl groups further comprise at least one ether group in the alkyl chain, and further wherein said alkenyl groups further comprise at least one ether group in the alkenyl chain.

93. The method according to claim 57, wherein said at least one fatty amide is chosen from behenamide, cetyl-PG hydroxyethyl decanamide, cetyl-PG hydroxyethyl palmitamide, cocamide, dibutyl lauroyl glutamide, distearyl phthalic acid amide, lauramide, lauroyl methyl glucamide, myristoyl-PG hydroxyethyl decanamide, oleyl palmitamide, stearamide, tallow amide, trideceth-2 carboxamide monoethanolamine (trideceth-2 carboxamide MEA), trideceth-2 carboxamide diethanolamine (trideceth-2 carboxamide DEA), trideceth-2 carboxamide monoisopropanolamine (trideceth-2 carboxamide MIPA), and polyalkoxylated fatty amides.

94. The method according to claim 93, wherein said polyalkoxylated fatty amides are chosen from polyethoxylated fatty amides and polyglycerylated fatty amides.

95. The method according to claim 57, wherein said at least one cationic homopolymer is present in an amount ranging from 0.05% to 10% by weight relative to the total weight of the composition.

96. The method according to claim 95, wherein said at least one cationic homopolymer is present in an amount ranging from 0.1% to 5% by weight relative to the total weight of the composition.

97. The method according to claim 96, wherein said at least one cationic homopolymer is present in an amount ranging from 0.25% to 2.5% by weight relative to the total weight of the composition.

98. The method according to claim 57, wherein said at least one fatty alcohol is present in an amount ranging from 0.05% to 10% by weight relative to the total weight of the composition.

99. The method according to claim 98, wherein said at least one fatty alcohol is present in an amount ranging from 0.1% to 8% by weight relative to the total weight of the composition.

100. The method according to claim 99, wherein said at least one fatty alcohol is present in an amount ranging from 0.2% to 4% by weight relative to the total weight of the composition.

101. The method according to claim 57, wherein said at least one alkoxylated fatty alcohol is present in an amount ranging from 0.05% to 10% by weight relative to the total weight of the composition.

102. The method according to claim 101, wherein said at least one alkoxylated fatty alcohol is present in an amount ranging from 0.1% to 5% by weight relative to the total weight of the composition.

103. The method according to claim 102, wherein said at least one alkoxylated fatty alcohol is present in an amount ranging from 0.2% to 2% by weight relative to the total weight of the composition.

104. The method according to claim 57, wherein said at least one fatty amide is present in an amount ranging from 0.05% to 10% by weight relative to the total weight of the composition.

105. The method according to claim 104, wherein said at least one fatty amide is present in an amount ranging from 0.1% to 8% by weight relative to the total weight of the composition.

106. The method according to claim 105, wherein said at least one fatty amide is present in an amount ranging from 0.2% to 4% by weight relative to the total weight of the composition.

107. The method according to claim 57, further comprising:
(e) at least one oxidizing agent,
wherein said at least one oxidizing agent is chosen from hydrogen peroxides, bromate salts, percarbonate salts, perborate salts and enzymes.

108. The method according to claim 57, further comprising:
(e) at least one oxidizing agent,
wherein said at least one oxidizing agent is present in an amount ranging from 0.1% to 20.0% by weight relative to the total weight of the composition.

109. The method according to claim 107, wherein said at least one oxidizing agent is present in an amount ranging from 0.5% to 12.0% by weight relative to the total weight of the composition.

110. A method for treating keratinous fibers comprising applying to said keratinous fibers at least one treatment composition comprising an oxidizing composition, wherein said oxidizing composition comprises:
(a) at least one cationic homopolymer comprising repeating units of formula (I):

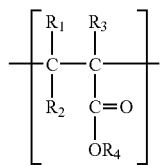

wherein:
$R_1$, $R_2$, and $R_3$, which may be identical or different, are each chosen from H, alkyl groups, and alkenyl groups; and
$R_4$ is chosen from groups comprising at least one quaternary amino group;
(b) at least one fatty alcohol;
(c) at least one alkoxylated fatty alcohol; and
(d) at least one fatty amide.

111. The method according to claim 110, wherein said at least one treatment composition is chosen from a dyeing composition, a bleaching composition, a permanent waving composition, and a relaxing composition.

112. The method according to claim 110, wherein said said at least one cationic homopolymer, said at least one fatty alcohol, said at least one alkoxylated fatty alcohol, and said at least one fatty amide are present in a combined amount effective to provide physical stability to said oxidizing composition.

113. The method according to claim 110, wherein said alkyl groups of $R_1$, $R_2$ and $R_3$ are chosen from linear $C_1$ to $C_{20}$ alkyl groups, branched $C_1$ to $C_{20}$ alkyl groups, and cyclic $C_1$ to $C_{20}$ alkyl groups, and further wherein said $C_1$ to $C_{20}$ alkyl groups are optionally substituted.

114. The method according to claim 110, wherein said alkenyl groups of $R_1$, $R_2$ and $R_3$ are chosen from linear $C_1$ to $C_{20}$ alkenyl groups, branched $C_1$ to $C_{20}$ alkenyl groups and cyclic $C_1$ to $C_{20}$ alkenyl groups, and further wherein said $C_1$ to $C_{20}$ alkenyl groups are optionally substituted.

115. The method according to claim 110, wherein $R_1$, $R_2$, and $R_3$ are each H.

116. The method according to claim 110, wherein $R_1$ is H, $R_2$ is H, and $R_3$ is $CH_3$.

117. The method according to claim 110, wherein, in the definition of $R_4$, said groups comprising at least one quaternary amino group are chosen from $C_1$ to $C_{20}$ alkyl quaternary amino groups.

118. The method according to claim 110, wherein in the definition of $R_4$, said groups comprising at least one quaternary amino group are chosen from compounds of formula (II):

wherein:
$R_5$, $R_6$ and $R_7$, which may be identical or different, are each chosen from H, alkyl groups, and alkenyl groups; and
$R_8$ is chosen from alkylene groups and alkenylene groups.

119. The method according to claim 118, wherein said alkyl groups of $R_5$, $R_6$, and $R_7$ are chosen from linear $C_1$ to $C_{20}$ alkyl groups, branched $C_1$ to $C_{20}$ alkyl groups and cyclic $C_1$ to $C_{20}$ alkyl groups, and further wherein said $C_1$ to $C_{20}$ alkyl groups are optionally substituted.

120. The method according to claim 119, wherein said alkenyl groups of $R_5$, $R_6$, and $R_7$ are chosen from linear $C_1$ to $C_{20}$ alkenyl chains, branched $C_1$ $C_{20}$ alkenyl chains and cyclic $C_1$ to $C_{20}$ alkenyl chains, and further wherein said $C_1$ to $C_{20}$ alkenyl groups are optionally substituted.

121. The method according to claim 119, wherein said alkylene groups of $R_8$ are chosen from linear $C_1$ to $C_{20}$ alkylene groups, branched $C_1$ to $C_{20}$ alkylene groups and cyclic $C_1$ to $C_{20}$ alkylene groups, and further wherein said $C_1$ to $C_{20}$ alkylene groups are optionally substituted.

122. The method according to claim 119, wherein said alkenylene groups of $R_8$ are chosen from linear $C_1$ to $C_{20}$ alkenylene chains, branched $C_1$ to $C_{20}$ alkenylene chains and cyclic $C_1$ to $C_{20}$ alkenylene chains, and further wherein said $C_1$ to $C_{20}$ alkenylene groups are optionally substituted.

123. The method according to claim 119, wherein said groups comprising at least one quaternary amino group are chosen from:

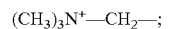

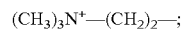

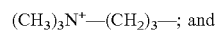

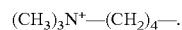

124. The method according to claim 119, wherein $R_5$ is a methyl group, $R_6$ is a methyl group, $R_7$ is an alkyl group chosen from linear unsubstituted $C_2$ to $C_{10}$ alkyl groups, and $R_8$ is an alkylene group chosen from linear unsubstituted $C_2$ to $C_{10}$ alkylene groups.

125. The method according to claim 119, wherein $R_5$, $R_6$, and $R_7$ are each a methyl group, and $R_8$ is an alkylene group chosen from linear $C_2$ to $C_{10}$ alkylene groups, branched $C_2$ to $C_{10}$ alkylene groups, and cyclic $C_2$ to $C_{10}$ alkylene groups.

126. The method according to claim 110, wherein said at least one cationic homopolymer is chosen from polyquaternium-37 homopolymers.

127. The method according to claim 110, wherein said at least one fatty alcohol comprises at least 8 carbon atoms.

128. The method according to claim 127, wherein said at least one fatty alcohol comprises at least 10 carbon atoms.

129. The method according to claim 128, wherein said at least one fatty alcohol comprises at least 12 carbon atoms.

130. The method according to claim 110, wherein said at least one fatty alcohol is chosen from $C_9$–$C_{11}$ alcohols, $C_{12}$–$C_{13}$ alcohols, $C_{12}$–$C_{15}$ alcohols, $C_{12}$–$C_{16}$ alcohols, and $C_{14}$–$C_{15}$ alcohols.

131. The method according to claim 110, wherein said at least one fatty alcohol is chosen from arachidyl alcohol, behenyl alcohol, caprylic alcohol, cetearyl alcohol, cetyl alcohol, coconut alcohol, decyl alcohol, hydrogenated tallow alcohol, jojoba alcohol, lauryl alcohol, myristyl alcohol, oleyl alcohol, palm alcohol, palm kernel alcohol, stearyl alcohol, tallow alcohol, and tridecyl alcohol.

132. The method according to claim 110, wherein said at least one alkoxylated fatty alcohol is chosen from fatty alcohols comprising at least one polyethylene glycol ether.

133. The method according to claim 110, wherein said at least one alkoxylated fatty alcohol comprises at least 8 carbon atoms.

134. The method according to claim 133, wherein said at least one alkoxylated fatty alcohol comprises at least 10 carbon atoms.

135. The method according to claim 134, wherein said at least one alkoxylated fatty alcohol comprises at least 12 carbon atoms.

136. The method according to claim 110, wherein said at least one alkoxylated fatty alcohol is chosen from ethoxylated fatty alcohols of formula

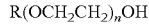

wherein:
R is chosen from linear alkyl groups comprising at least 5 carbon atoms, branched alkyl groups comprising at least 5 carbon atoms, and cyclic alkyl groups comprising at least 5 carbon atoms, wherein said alkyl groups are optionally substituted; and linear alkenyl groups comprising at least 5 carbon atoms, branched alkenyl groups comprising at least 5 carbon atoms, and cyclic alkenyl groups comprising at least 5 carbon atoms, wherein said alkenyl groups are optionally substituted; and
n ranges from 2 to 100.

137. The method according to claim 136, wherein R is chosen from linear $C_8$ to $C_{22}$ alkyl groups, branched $C_8$ to $C_{22}$ alkyl groups, and cyclic $C_8$ to $C_{22}$ alkyl groups.

138. The method according to claim 136, wherein R is chosen from linear $C_8$ to $C_{22}$ alkenyl groups, branched $C_8$ to $C_{22}$ alkenyl groups, and cyclic $C_8$ to $C_{22}$ alkenyl groups.

139. The method according to claim 110, wherein said at least one alkoxylated fatty alcohol is chosen from alkoxy esters of polyglyceryl of the formula

and alkoxy esters of polyglyceryl of the formula

wherein:
R is chosen from linear alkyl groups comprising at least 5 carbon atoms, branched alkyl groups comprising at least 5 carbon atoms, and cyclic alkyl groups comprising at least 5 carbon atoms, wherein said alkyl groups are optionally substituted; and linear alkenyl groups comprising at least 5 carbon atoms, branched alkenyl groups comprising at least 5 carbon atoms, and cyclic alkenyl groups comprising at least 5 carbon atoms, wherein said alkenyl groups optionally substituted;

R' is chosen from H; linear alkyl groups comprising at least 5 carbon atoms, branched alkyl groups comprising at least 5 carbon atoms, and cyclic alkyl groups comprising at least 5 carbon atoms, wherein said alkyl groups optionally substituted; and linear alkenyl groups comprising at least 5 carbon atoms, branched alkenyl groups comprising at least 5 carbon atoms, and cyclic alkenyl groups comprising at least 5 carbon atoms, wherein said alkenyl groups are optionally substituted; and n ranges from 1 to 30, with the proviso that at least one of said R' is chosen from linear alkyl groups comprising at least 5 carbon atoms, branched alkyl groups comprising at least 5 carbon atoms, and cyclic alkyl groups comprising at least 5 carbon atoms, wherein said alkyl groups are optionally substituted, and linear alkenyl groups comprising at least 5 carbon atoms, branched alkenyl groups comprising at least 5 carbon atoms, and cyclic alkenyl groups comprising at least 5 carbon atoms, wherein said alkenyl groups are optionally substituted.

140. The method according to claim 139, wherein R is chosen from linear $C_8$ to $C_{22}$ alkyl groups, branched $C_8$ to $C_{22}$ alkyl groups, and cyclic $C_8$ to $C_{22}$ alkyl groups.

141. The method according to claim 139, wherein R is chosen from linear $C_8$ to $C_{22}$ alkenyl groups, branched $C_8$ to $C_{22}$ alkenyl groups, and cyclic $C_8$ to $C_{22}$ alkenyl groups.

142. The method according to claim 110, wherein said at least one alkoxylated fatty alcohol is chosen from ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceteareth-33, ceteareth-34, ceteareth-40, ceteareth-50, ceteareth-55, ceteareth-60, ceteareth-80, ceteareth-100, laureth-1, laureth-2, laureth-3, laureth-4, laureth-5, laureth-6, laureth-7, laureth-8, laureth-9, laureth-10, laureth-11, laureth-12, laureth-13, laureth-14, laureth-15, laureth-16, laureth-20, laureth-23, laureth-25, laureth-30, laureth-40, deceth-3, deceth-5, oleth-5, oleth-30, steareth-2, steareth-10, steareth-20, steareth-100, cetylsteareth-12, ceteareth-5, ceteareth-5, polyglyceryl 4-lauryl ether, polyglyceryl 4-oleyl ether, polyglyceryl 2-oleyl ether, polyglyceryl 2-cetyl ether, polyglyceryl 6-cetyl ether, polyglyceryl 6-oleylcetyl ether, polyglyceryl 6-octadecyl ether, $C_9$–$C_{11}$ pareth-3, $C_9$–$C_{11}$ pareth-6, $C_{11}$–$C_{15}$ pareth-3, $C_{11}$–$C_{15}$ pareth-5, $C_{11}$–$C_{15}$ pareth-12, $C_{11}$–$C_{15}$ pareth-20, $C_{12}$–$C_{15}$ pareth-9, $C_{12}$–$C_{15}$ pareth-12, and $C_{22}$–$C_{24}$ pareth-33.

143. The method according to claim 110, wherein said at least one fatty amide is chosen from fatty amides of formula

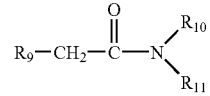

wherein:

R$_9$ is chosen from linear alkyl groups comprising at least 4 carbon atoms, branched alkyl groups comprising at least 4 carbon atoms, and cyclic alkyl groups comprising at least 4 carbon atoms, wherein said alkyl groups are optionally substituted; linear alkenyl groups comprising at least 4 carbon atoms, branched alkenyl groups comprising at least 4 carbon atoms, and cyclic alkenyl groups comprising at least 4 carbon atoms, wherein said alkenyl groups are optionally substituted; and alkoxylated alkyl groups of formulae

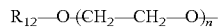

and

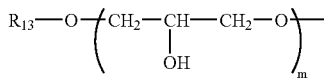

wherein:

R$_{12}$ and R$_{13}$, which may be identical or different, are each chosen from linear alkyl groups comprising at least 4 carbon atoms, branched alkyl groups comprising at least 4 carbon atoms, and cyclic alkyl groups comprising at least 4 carbon atoms, wherein said alkyl groups are optionally substituted; and linear alkenyl groups comprising at least 4 carbon atoms, branched alkenyl groups comprising at least 4 carbon atoms, and cyclic alkenyl groups comprising at least 4 carbon atoms, wherein said alkenyl groups are optionally substituted;

n ranges from 1 to 10; and m ranges from 1 to 6; and

R$_{10}$, and R$_{11}$, which may be identical or different, are each chosen from H; linear alkyl groups, branched alkyl groups and cyclic alkyl groups, wherein said alkyl groups are optionally substituted; and linear alkenyl groups, branched alkenyl groups and cyclic alkenyl groups, wherein said alkenyl groups are optionally substituted.

144. The method according to claim 143, wherein R$_9$ is chosen from linear C$_8$ to C$_{22}$ alkyl groups, branched C$_8$ to C$_{22}$ alkyl groups and cyclic C$_8$ to C$_{22}$ alkyl groups, wherein said C$_8$ to C$_{22}$ alkyl groups are optionally substituted; and linear C$_8$ to C$_{22}$ alkyl groups, branched C$_8$ to C$_{22}$ alkyl groups and cyclic C$_8$ to C$_{22}$ alkenyl groups, wherein said C$_8$ to C$_{22}$ alkyl groups are optionally substituted.

145. The method according to claim 143, wherein R$_{10}$ and R$_{11}$ are each chosen from linear C$_1$ to C$_{22}$ alkyl groups, branched C$_1$ to C$_{22}$ alkyl groups and cyclic C$_1$ to C$_{22}$ alkyl groups, wherein said C$_1$ to C$_{22}$ alkyl groups are optionally substituted; and linear C$_1$ to C$_{22}$ alkenyl groups, branched C$_1$ to C$_{22}$ alkenyl groups and cyclic C$_1$ to C$_{22}$ alkenyl groups, wherein said C$_1$ to C$_{22}$ alkenyl groups are optionally substituted.

146. The method according to claim 143, wherein at least one of said R$_{10}$ and said R$_{11}$ is chosen from linear C$_1$ to C$_{22}$ alkyl groups, branched C$_1$ to C$_{22}$ alkyl groups and cyclic C$_1$ to C$_{22}$ alkyl groups; and linear C$_1$ to C$_{22}$ alkenyl groups, branched C$_1$ to C$_{22}$ alkenyl groups and cyclic C$_1$ to C$_{22}$ alkenyl groups, wherein said alkyl groups and said alkenyl groups are substituted with at least one hydroxyl group.

147. The method according to claim 143, wherein at least one of said R$_{10}$ and R$_{11}$ is chosen from linear C$_1$ to C$_{22}$ alkyl groups, branched C$_1$ to C$_{22}$ alkyl groups and cycle C$_1$ to C$_{22}$ alkyl groups; and linear C$_1$ to C$_{22}$ alkenyl groups, branched C$_1$ to C$_{22}$ alkenyl groups and cyclic C$_1$ to C$_{22}$ alkenyl groups, wherein said alkyl groups further comprise at least one ether group in the alkyl chain, and further wherein said alkenyl groups further comprise at least one ether group in the alkenyl chain.

148. The method according to claim 110, wherein said at least one fatty amide is chosen from behenamide, cetyl-PG hydroxyethyl decanamide, cetyl-PG hydroxyethyl palmitamide, cocamide, dibutyl lauroyl glutamide, distearyl phthalic acid amide, lauramide, lauroyl methyl glucamide, myristoyl-PG hydroxyethyl decanamide, oleyl palmitamide, stearamide, tallow amide, trideceth-2 carboxamide monoethanolamine (trideceth-2 carboxamide MEA), trideceth-2 carboxamide diethanolamine (trideceth-2 carboxamide DEA), trideceth-2 carboxamide monoisopropanolamine (trideceth-2 carboxamide MIPA), and polyalkoxylated fatty amides.

149. The method according to claim 148, wherein said polyalkoxylated fatty amides are chosen from polyethoxylated fatty amides and polyglycerylated fatty amides.

150. The method according to claim 110, wherein said at least one cationic homopolymer is present in an amount ranging from 0.05% to 10% by weight relative to the total weight of the composition.

151. The method according to claim 150, wherein said at least one cationic homopolymer is present in an amount ranging from 0.1% to 5% by weight relative to the total weight of the composition.

152. The method according to claim 151, wherein said at least one cationic homopolymer is present in an amount ranging from 0.25% to 2.5% by weight relative to the total weight of the composition.

153. The method according to claim 110, wherein said at least one fatty alcohol is present in an amount ranging from 0.05% to 10% by weight relative to the total weight of the composition.

154. The method according to claim 153, wherein said at least one fatty alcohol is present in an amount ranging from 0.1% to 8% by weight relative to the total weight of the composition.

155. The method according to claim 154, wherein said at least one fatty alcohol is present in an amount ranging from 0.2% to 4% by weight relative to the total weight of the composition.

156. The method according to claim 110, wherein said at least one alkoxylated fatty alcohol is present in an amount ranging from 0.05% to 10% by weight relative to the total weight of the composition.

157. The method according to claim 156, wherein said at least one alkoxylated fatty alcohol is present in an amount ranging from 0.1% to 5% by weight relative to the total weight of the composition.

158. The method according to claim 157, wherein said at least one alkoxylated fatty alcohol is present in an amount ranging from 0.2% to 2% by weight relative to the total weight of the composition.

159. The method according to claim 110, wherein said at least one fatty amide is present in an amount ranging from 0.05% to 10% by weight relative to the total weight of the composition.

160. The method according to claim 159, wherein said at least one fatty amide is present in an amount ranging from 0.1% to 8% by weight relative to the total weight of the composition.

161. The method according to claim 160, wherein said at least one fatty amide is present in an amount ranging from 0.2% to 4% by weight relative to the total weight of the composition.

162. The method according to claim 110, further comprising:
(e) at least one oxidizing agent,
wherein said at least one oxidizing agent is chosen from hydrogen peroxides, bromate salts, percarbonate salts, perborate salts and enzymes.

163. The method according to claim 110, further comprising:
(e) at least one oxidizing agent,
wherein said at least one oxidizing agent is present in an amount ranging from 0.1% to 20.0% by weight relative to the total weight of the composition.

164. The method according to claim 163, wherein said at least one oxidizing agent is present in an amount ranging from 0.5% to 12.0% by weight relative to the total weight of the composition.

165. The method according to claim 110, wherein said keratinous fibers are chosen from hair, eyelashes, and eyebrows.

166. A multi-compartment kit for treating keratinous fibers, said kit comprising at least two separate compartments, wherein
a first compartment comprises an oxidizing composition, said oxidizing composition comprising:
(a) at least one cationic homopolymer comprising repeating units of formula (I):

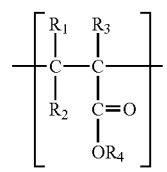

wherein:
$R_1$, $R_2$, and $R_3$, which may be identical or different, are each chosen from H, alkyl groups, and alkenyl groups; and
$R_4$ is chosen from groups comprising at least one quaternary amino group;
(b) at least one fatty alcohol;
(c) at least one alkoxylated fatty alcohol;
(d) at least one fatty amide; and
a second compartment comprising a composition for treating said keratinous fibers.

167. A multi-compartment kit according to claim 166, wherein said composition for treating said keratinous fibers is chosen from al dyeing composition, a bleaching composition, a permanent waving composition, and a relaxing composition.

168. A multi-compartment kit according to claim 166, wherein said keratinous fibers are chosen from hair, eyelashes, and eyebrows.

* * * * *

UNITED STATES PATENT AND TRADEMARK OFFICE
CERTIFICATE OF CORRECTION

PATENT NO. : 7,204,855 B2 Page 1 of 1
APPLICATION NO. : 09/881807
DATED : April 17, 2007
INVENTOR(S) : Ascione et al.

It is certified that error appears in the above-identified patent and that said Letters Patent is hereby corrected as shown below:

Claim 1, col. 11, line 25, insert "1:" after "formula".

Claim 167, col. 30, line 26, "al" should read --a--.

Signed and Sealed this

Third Day of July, 2007

JON W. DUDAS
*Director of the United States Patent and Trademark Office*